(12) United States Patent
Duchek

(10) Patent No.: US 7,402,686 B2
(45) Date of Patent: Jul. 22, 2008

(54) CANNABINOID CRYSTALLINE DERIVATIVES AND PROCESS OF CANNABINOID PURIFICATION

(75) Inventor: John Robert Duchek, St. Louis, MO (US)

(73) Assignee: Mallinckrodt Inc., Hazelwood, MO (US)

( * ) Notice: Subject to any disclaimer, the term of this patent is extended or adjusted under 35 U.S.C. 154(b) by 237 days.

(21) Appl. No.: 10/533,576

(22) PCT Filed: Nov. 6, 2003

(86) PCT No.: PCT/US03/35599

§ 371 (c)(1),
(2), (4) Date: May 3, 2005

(87) PCT Pub. No.: WO2004/043946

PCT Pub. Date: May 27, 2004

(65) Prior Publication Data

US 2006/0094774 A1 May 4, 2006

Related U.S. Application Data

(60) Provisional application No. 60/435,027, filed on Dec. 20, 2002, provisional application No. 60/425,543, filed on Nov. 12, 2002.

(51) Int. Cl.
*C07D 311/80* (2006.01)
(52) U.S. Cl. ...................................... 549/390
(58) Field of Classification Search .................. 549/390
See application file for complete search history.

(56) References Cited

U.S. PATENT DOCUMENTS

| | | |
|---|---|---|
| 3,507,888 A | 4/1970 | Fahrenholtz |
| 3,636,058 A | 1/1972 | Fahrenholtz |
| 3,728,360 A | 4/1973 | Pars et al. |
| 4,188,495 A | 2/1980 | Althuis et al. |
| 4,206,225 A | 6/1980 | Johnson |
| 4,341,906 A | 7/1982 | Althuis et al. |
| 4,381,399 A | 4/1983 | Olsen et al. |
| 5,637,738 A | 6/1997 | Blacker et al. |
| 6,008,383 A | 12/1999 | Elsohly et al. |

FOREIGN PATENT DOCUMENTS

WO  WO 2006/000734  1/2006

OTHER PUBLICATIONS

Maseda, Chikatoshi et al; "Stability and Hydrolysis of Dabsylcannabinoids"; Article; 1985; pp. 11-15; XP-001180138; Department of Legal Medicine, Shimane Medical University, Izumo, Japan.
Maseda, Chikatoshi et al; "Chromophoric Labeling of Cannabinoids with 4-Dimethylaminoazobenzene-4'—Sulfonyl Chloride"; Article; 1983 pp. 911-921; Journal of Forensic Sciences, vol. 28, No. 4, XP009027721; Izumo, Japan.
Watanabe, Kazuhito et al; "Synthesis of $\Delta^8$-Tetrahydrocannabinol Glucuronide and Sulfate, and Their Metabolic Disposition in Rats"; Article; May 1979; pp. 3009-3014; XP001180085; Faculty of Pharmaceutical Sciences, Kyushu University.
R. Adams et al. "Structure of Cannabinol. I. Preparation of an Isomer, 3-Hydroxy-1-n-amyl-6,6,9-trimethyl-6-dibenzopyran"; Article; Aug. 1940; pp. 2197-2200; Journal of the American Chemical Society, vol. 62, XP-002274652; U.S.
Robert Sidney Cahn; "Cannabis Indica Resin. Part III. The Constitution of Cannabinol"; Article; 1932; pp. 1342-1357; XP009027717; The University Chemical Laboratory, Cambridge.
Fahrenholtz, Kenneth E. et al.; "The Total Synthesis of dl-$\Delta^9$-Tetrahydrocannabinol and Four of Its Isomers"; Article; Nov. 1967; pp. 5934-5941; Journal of the American Chemical Society, XP-002274651; U.S.
Melikian, Armen P. et al. "Dansyl Derivatives of $\Delta^9$- and $\Delta^8$-Tetrahydrocannabinols"; Article; Jun. 1973; pp. 1025-1026; Journal of Pharmaceutical Sciences, vol. 62, No. 6, XP009027720; U.S.
Merck Index, "Tetrahydrocannabinols"; Entry 9349; p. 1573; 12th Edition.

*Primary Examiner*—Bernard Dentz
(74) *Attorney, Agent, or Firm*—Sarah Pfeifer Vaz; Husch Blackwell Sanders LLP

(57) ABSTRACT

$\Delta 9$ tetrahydrocannabinol (THC) esters comprising the reaction product of THC with at least one aryl sulfonyl chloride in the presence of at least one tertiary amine. The resulting aryl sulfonic THC esters are highly crystalline and stable at room temperature in air, allowing for indefinite storage. The aryl sulfonic THC esters can be recrystallized for purification, and then hydrolyzed to recover the purified THC.

15 Claims, No Drawings

CANNABINOID CRYSTALLINE DERIVATIVES AND PROCESS OF CANNABINOID PURIFICATION

CROSS REFERENCE TO RELATED APPLICATIONS

This application is a national stage application of PCT/US03/35599, filed Nov. 6, 2003, which claims the benefit of U.S. Provisional Application Ser. No. 60/425,543 filed Nov. 12, 2002, and U.S. Provisional Application Ser. No. 60/435,027, filed Dec. 20, 2002.

FIELD OF THE INVENTION

The present invention relates to cannabinoid crystalline derivatives and more particularly to cannabinoid-aryl sulfonates that can be utilized for purification and/or storage of cannabinoid compounds.

BACKGROUND OF THE INVENTION

Naturally occurring cannabinoids are the biologically active components of cannabis. Pharmaceutical interest in cannabinoids has increased due to FDA approval of $\Delta^9$-tetrahydrocannabinol (THC) for several therapeutic applications. This interest has lead to the development of synthetic cannabinoid compounds.

In general, both natural and synthetic cannabinoids are very difficult molecules to work with, as they tend to be hard glasses that are prone to oxidation at room temperature. THC is a non-crystalline glass at room temperature, and is susceptible to rearrangement and air oxidation. Although THC is typically stored in a dark freezer under an inert gas, maintaining purity during storage is very difficult. These characteristics also complicate the use of cannabinoids as reactants in other synthesis methods or uses.

Purification of cannabinoids is also complicated by the characteristics listed above. Furthermore, many of the impurities commonly found in cannabinoid mixtures are also problematic. Conventional methods of purification typically involve the use of HPLC. These methods are inconvenient and expensive, and make scaling up of the purification process impractical.

It is therefore desirable to provide a method for producing a cannabinoid derivative that allows for ease in handling, stable storage, an improved method of purification, and that are easily converted back to a cannabinoid.

SUMMARY OF THE INVENTION

An aspect of the present invention is to provide cannabinoid aryl sulfonates including those represented by the formula

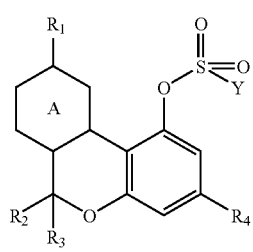

Formula A wherein $R_1$, $R_2$, $R_3$, and $R_4$ are H or an alkyl;

A is a saturated alkane, alkene, diene forming a six membered fused ring or an aromatic ring; and Y is an aryl.

A further aspect of the present invention is to provide a process for the preparation of cannabinoid esters comprising reacting cannabinoid with at least one aryl sulfonyl halide in the presence of at least one base.

Another aspect of the present invention is to provide a process for the purification of cannabinoid comprising esterifying the cannabinoid with at least one aryl sulfonyl halide in the presence of at least one base to form cannabinoid aryl sulfonate, crystallizing the cannabinoid aryl sulfonate, and hydrolyzing the cannabinoid aryl sulfonate to recover the cannabinoid. The cannabinoid aryl sulfonate crystals may be recrystallized to purify the cannabinoid aryl sulfonate.

These are merely illustrative aspects of the present invention and should not be deemed an all-inclusive listing of the innumerable aspects associated with the present invention. These and other aspects will become apparent to those skilled in the art in light of the following disclosure.

DETAILED DESCRIPTION

There is provided a process for the esterification of cannabinoids according to the reaction as follows:

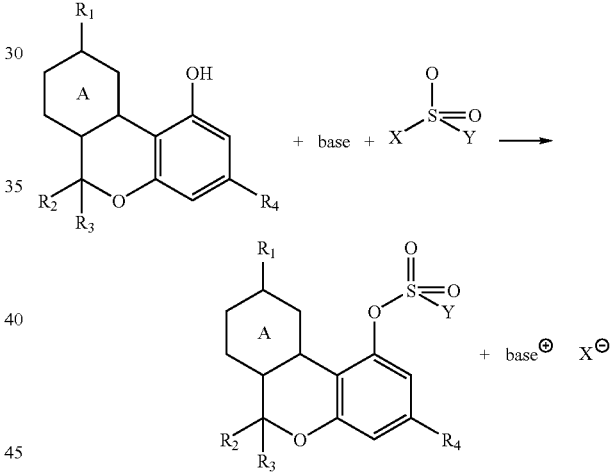

Reaction 1 wherein $R_1$, $R_2$, $R_3$, and $R_4$ are H or an alkyl;

A is a saturated alkane, alkene, diene or aromatic ring; Y is an aryl and X is a halide.

Impure cannabinoids can be treated with at least one aryl sulfonyl halide in the presence of at least one base to cause reaction at the phenol hydroxy group thereby producing aryl sulfonates.

The base is added to take up the halide acid produced by the esterification. Therefore, any suitable base that does not interfere with the esterification reaction may be used. Lower alkyl amines, especially tertiary amines such as triethyl amine provide inexpensive bases that are suitable for the present invention. Primary and secondary amines may be used, but will result in unwanted reactions with the sulfonyl halide. Amines of the formula $R_5R_6R_7N$ are preferred wherein $R_5$, $R_6$ and $R_7$ may typically be lower alkyl radicals having from about one to about six carbon atoms.

The aryl group of the sulfonyl halide may be any aromatic system, substituted or unsubstituted, that does not interfere with the esterification reaction. Suitable aromatic systems include but are not limited to benzene, alkyl substituted benzene, halogen substituted benzene, nitrobenzene, alkyloxy substituted benzene and substituted and unsubstituted napthyl compounds. Preferred alkoxy substituents include an alkoxide directly attached to a tertiary carbon wherein the alkyloxy substituent may typically be from about one to about six carbon atoms.

In a preferred embodiment, the cannabinoid, aryl sulfonyl halide and a tertiary amine are mixed in an organic solvent and allowed to react at room temperature until completion, typically several hours. The choice of solvent is not critical, and suitable solvents include, but are not limited to toluene, methylene chloride, chloroform and heptane. In an alternative embodiment, the reaction may be run at increased temperatures without affecting the efficacy of the reaction, although with minimal increase in reaction rate. Temperatures in the range of from about room temperature to about 80° C. are typical.

The solvent is then removed by any suitable method so that the cannabinoid aryl sulfonate forms an oil that can then be crystallized. The crystallization can be aided by the addition of a solvent and seed crystals, as is well known in the art. Suitable solvents include, but are not limited to, heptane, hexane, t-butyl methyl ether, n-pentanol, n-butanol, isopropanol, isobutanol, ethanol, acetone, acetonitrile and isopropyl acetate. Alcohols, including methanol are preferred. In general the purity of this crude crystalline ester will be well over 90% pure. About 70 to 80% of the initially assayed cannabinoid can be obtained in the first crop of crystals. Purification of up to greater than 99% can typically be achieved by one recrystallization, preferable from an alcohol, with minimal losses in yield. (All percentages given herein are weight percentages unless otherwise noted.) The resulting cannabinoid esters are highly crystalline and stable at room temperature. They can be stored indefinitely at room temperature under air.

The cannabinoid esters can then be hydrolyzed to recover the pure cannabinoid by base hydrolysis, as is shown in the reaction below:

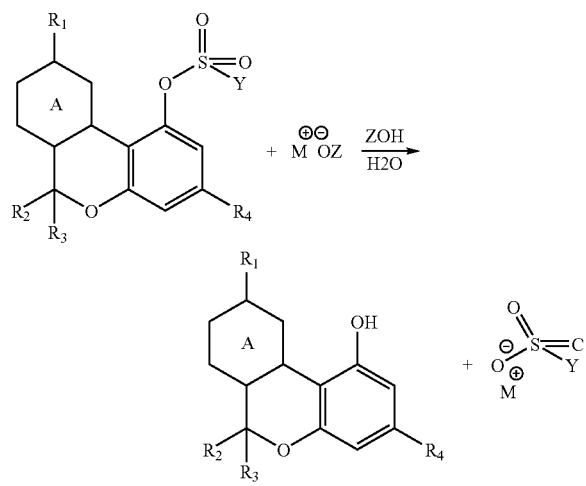

Reaction 2 wherein $R_1$, $R_2$, $R_3$, and $R_4$ are H or an alkyl;

A is a saturated alkane, alkene, diene or aromatic ring,

Y is an aryl, M is a metal and Z is an alkyl, typically 1 C to 10 C.

The hydrolysis can be accomplished by any method known in the art. In a preferred embodiment the base comprises at least one metal salt of an alkyl oxide in at least one alkyl alcohol. Suitable bases include but are not limited to potassium methoxide, ethoxide, propoxide, isopropoxide, t-butoxide and t-pentanoxide, with tertiary alkoxides preferred. Suitable alcohols include but are not limited to methanol, ethanol, n-propanol, isopropanol, t-butanol and t-pentanol, with tertiary alkoxides preferred. The use of the same alkyl group for both the oxide and the alcohol is preferred to prevent exchange of the groups, for example, potassium t-butoxide in t-butanol with several equivalents of water added. The reaction preferably includes at least 3 equivalents of base and at least 4 equivalents of water per equivalent of cannabinoid used. The reaction is preferably run at a temperature of at least 40° C. The purity of the recovered cannabinoid typically exceeds 99%, with 85% to 95% yields. Alkyl oxides and alcohols typically contain alkyl groups of one to about six carbon atoms for practical purposes, although larger alkyl groups may be used.

A suitable method of hydrolysis is comprised of placing the tosylate in a three-necked flask under an inert atmosphere. The flask is typically equipped for magnetic stirring and electronic temperature control, with a condenser, inert gas bubbler and a heating mantle. Deionized water and then an alkyl oxide in alcohol are added to the flask. All solvents utilized are deoxygenated by bubbling with an inert gas. In one embodiment, the resulting slurry is then heated to at least about 40° C. to increase the reaction rate and to force the reaction to completion. While the reaction will proceed at lower temperatures, the reaction is preferably heated to about 40° C. to about 80° C., with about 50° C. to about 70° C. being optimum, the maximum temperature being determined by the boiling point of the solvent being used. The reaction mixture is maintained at the desired temperature until the reaction is substantially complete, typically about two to twelve hours, and then cooled to room temperature.

Deionized water is added, and the reaction stirred. An organic solvent is added, and the resulting mixture stirred or agitated and placed in a separatory funnel and separated. The organic fraction containing the cannabinoid product is then washed with at least one aliquot of deionized deoxygenated water. The organic fraction is then typically dried with a salt solution, filtered and evaporated under vacuum to form an oil. Distillation of the resulting oil under high vacuum results in a highly purified cannabinoid product.

The following examples are offered to illustrate aspect is of the present invention, and are not intended to limit or define the present invention in any manner.

EXAMPLE 1

Synthesis of $\Delta^9$-tetrahydrocannabinol tosylate 64.9 g of $\Delta^9$-tetrahydrocannabinol, 292 mL of toluene, 21.7 mL of triethyl amine, and 41.3 g. of p-toluene sulfonyl chloride were added to a 1000 mL, 3 neck, round bottom flask blanketed with nitrogen. The reaction was stirred overnight at room temperature for about 16 hours. The reaction was checked by LC and was found to be complete. Water (292 mLs) was added, and the reaction was stirred for 20 minutes. The aqueous layer was separated, and the toluene solution was washed two more times with 292 mL aliquots of water. The toluene was washed with 292 mL of saturated sodium chloride solution to aid water removal, and the toluene was then dried with anhydrous magnesium sulfate. The dry toluene solution was evaporated on an evaporator down to an oil 99.76 g. The oil was poured into 500 mL Erlenmeyer flask and 150 mL of heptane was added. The solution was seeded with a few crystals from an earlier run and stored in a refrigerator overnight. The resulting solids were filtered. The crystals were washed twice with approximately 10 mL aliquots of chilled heptane while on the filter. The crystals were dried under vacuum for 15 minutes on the Buchner funnel and weighed. The slightly wet crystals weighed 65.4 grams. After drying overnight at room temperature in a 23" Hg vacuum the crystals weighed 65.37 g. A second crop of crystals, 6.34 g. was obtained by evaporating most of the heptane and chilling the mother liquor overnight under refrigeration.

The crystals were dissolved in 440 mL of hot methanol at reflux. The crystals dissolved easily at 66° C. The flask was allowed to cool slowly towards room temperature and crystallization commenced at 51° C. The flask was then chilled to near 0° C. in an ice-bath while fresh methanol was chilled as a wash. The flask was held at 0° C. for 1.5 hours and the slurry was then filtered. The solids were washed with a total of 110 mL of cold methanol in two washes. The wet weight of the crystals was 64.09 g. The crystals were dried in a 23" vacuum at room temperature over a weekend. The dried crystals weighed 62.64 g. Unlike the free Δ9-tetrahydrocannabinol, the tosylate derivative has been shown to be stable at room temperature in the presence of air and laboratory lighting. The $\Delta^9$ THC-4-methylbenzene sulfonate (tosylate) crystals were characterized by IF, proton NMR, C13 NMR and MS methods. The infrared spectrum for the tosylate was consistent with that for $\Delta^9$ THC, with additional bands for the organic sulfonate functionality. NMR analysis strongly supports the structure of Δ9 THC-4-methylbenzene sulfonate (tosylate). Mass spectral results show the major component to have a molecular weight of 468 Da that is consistent with the molecular weight of $\Delta^9$ THC-4-methylbenzene sulfonate (tosylate). Further, the MS/MS fragmentation pattern is also consistent with the identification of the major component as $\Delta^9$ THC-4-methylbenzene sulfonate (tosylate).

EXAMPLE 2

$\Delta^9$-tetrahydrocannabinol-benzenesulfonate crystals were formed as in Example 1 utilizing benzene sulfonyl chloride in place of p-toluene sulfonyl chloride. The resulting crystals were stable at room temperature in the presence of air and laboratory lighting.

EXAMPLE 3

$\Delta^9$-tetrahydrocannabinol-4-methoxybenzene sulfonate crystals were formed as in Example 1 utilizing 4-methoxybenzene sulfonyl chloride in place of p-toluene sulfonyl chloride. The resulting crystals were stable at room temperature in the presence of air and laboratory lighting.

EXAMPLE 4

$\Delta^9$-tetrahydrocannabinol-4-bromobenzenesulfonate crystals were formed as in Example 1 utilizing 4-bromobenzene sulfonyl chloride in place of p-toluene sulfonyl chloride. The resulting crystals were stable at room temperature in the presence of air and laboratory lighting.

EXAMPLE 5

$\Delta^9$-tetrahydrocannabinol4-chlorobenzenesulfonate crystals were formed as in Example 1 utilizing 4-chlorobenzene sulfonyl chloride in place of p-toluene sulfonyl chloride. The resulting crystals were stable at room temperature in the presence of air and laboratory lighting.

EXAMPLE 6

$\Delta^9$-tetrahydrocannabinol-2-nitrobenzenesulfonate crystals were formed as in Example 1 utilizing 2-nitrobenzene sulfonyl chloride in place of p-toluene sulfonyl chloride. The resulting crystals were stable at room temperature in the presence of air and laboratory lighting.

EXAMPLE 7

$\Delta^9$-tetrahydrocannabinol-3-nitrobenzenesulfonate crystals were formed as in Example 1 utilizing 3-nitrobenzene sulfonyl chloride in place of p-toluene sulfonyl chloride. The resulting crystals were stable at room temperature in the presence of air and laboratory lighting.

EXAMPLE 8

$\Delta^9$-tetrahydrocannabinol-4-nitrobenzenesulfonate was formed as in Example 1 utilizing 4-nitrobenzene sulfonyl chloride in place of p-toluene sulfonyl chloride, except the resulting oil did not crystallize.

EXAMPLE 9

$\Delta^9$-tetrahydrocannabinol-1-napthylsulfonate was formed as in Example 1 utilizing 1-napthyl sulfonyl chloride in place of p-toluene sulfonyl chloride, except the resulting oil did not crystallize.

EXAMPLE 10

$\Delta^9$-tetrahydrocannabinol-2-napthylsulfonate was formed as in Example 1 utilizing 2-napthyl sulfonyl chloride in place of p-toluene sulfonyi chloride; except the resulting oil did not crystallize.

EXAMPLE 11

$\Delta^8$-tetrahydrocannabinol-4-methylbenzenesulfonate crystals were formed as in Example 1 utilizing $\Delta^8$-tetrahydrocannabinol in place of $\Delta^9$-tetrahydrocannabinol. The resulting crystals were stable at room temperature in the presence of air and laboratory lighting.

EXAMPLE 12

Cannabinol-4-methylbenzenesulfonate crystals were formed as in Example 1 utilizing Cannabinol in place of Δ9-tetrahydrocannabinol. The resulting crystals were stable at room temperature in the presence of air and laboratory lighting.

EXAMPLE 13

Hydrolysis of $\Delta^9$-tetrahydrocannabinol tosylate to free $\Delta^9$-tetrahydrocannabinol Twenty-five grams of purified $\Delta^9$-tetrahydrocannabinol-4-methylbenzene sulfonate (tosylate) assayed at 99+% pure was placed into a 500 mL, 3 neck, round bottomed flask under a nitrogen blanket. The flask was equipped for magnetic stirring, electronic temperature control, with a condenser, nitrogen bubbler, and a heating mantle.

All solvents utilized were deoxygenated by bubbling N2 through them for 15 minutes prior to use. 3.9 mLs of deionized water was added and then 162.5 mLs of 1 molar potassium butoxide in t-butanol (note 1) was added to the flask. The resulting slurry was heated to 65° C. The reaction was slightly exothermic, raising the temperature to 70.1° C., but settled back to 65° C., quickly. The reaction was held at 65° C. for 5 hours, and then cooled to room temperature.

Water (250 mLs) was added and the reaction was stirred for 1.0 hour. It is anticipated that this process destroys a small amount of t-butyl tosylate that is formed in the reaction. Heptane (250 mLs) is then added. After stirring for several minutes, the mixture is transferred to a separatory funnel (1000 mL) and separated. (A small amount of water may be added if a small third phase of t-butanol is noted.) The heptane solution containing the cannabinoid product is washed 2 more times with 250 mL aliquots of deionized deoxygenated water. The pH of the first wash was 14, the second wash pH 9 and the third was pH 8.

A preliminary drying was done by washing the heptane solution with 250 mL of saturated sodium chloride solution.

The heptane was then dried with anhydrous $MgSO_4$. The solution was filtered and evaporated under vacuum to an oil (16.68 g.).

The oil was distilled under high vacuum <2 mm Hg at about 200°-220° C. A nearly colorless glass was obtained and weighed 15.41 g., and 88% yield.

LC analysis of the product showed that it was >99.9 area % $\Delta^9$-tetrahydrocannabinol. Comparison with a purchased standard material showed a purity of 104%. The product was scrupulously protected from light and oxygen and stored in a freezer to maintain this purity.

Having described the invention in detail, those skilled in the art will appreciate that modifications may be made of the invention without departing from its spirit and scope. Therefore, it is not intended that the scope of the invention be limited to the specific embodiments described. Rather, it is intended that the appended claims and their equivalents determine the scope of the invention.

What is claimed is:

1. A process for the preparation of cannabinoid aryl sulfonates comprising:
   reacting at least one cannabinoid with at least one aryl sulfonyl halide in the presence of at least one base $R_5R_6R_7N$, wherein $R_5$, $R_6$ and $R_7$ are lower alkyls of 1 to about 6 carbon atoms, and a solvent, wherein the cannabinoid aryl sulfonates are crystalline and stable at room temperature under air.

2. The process according to claim 1, wherein the cannabinoid is a naturally occurring component of cannabis.

3. The process according to claim 1, wherein the aryl of the at least one aryl sulfonyl halide is selected from the group consisting of benzene, alkyl substituted benzene, halogen substituted benzene, nitrobenzene, alkyloxy substituted benzene, substituted naphthyl compounds and unsubstituted naphthyl compounds.

4. The process according to claim 1, further including mixing the at least one cannabinoid, the at least one aryl sulfonyl halide and the at least one base in an organic solvent prior to the reacting of the at least one cannabinoid with the at least one aryl sulfonyl halide in the presence of the at least one base and further includes removing the organic solvent after the step of reacting the at least one cannabinoid with the at least one aryl sulfonyl halide in the presence of the at least one base.

5. The process according to claim 4, wherein the organic solvent is selected from the group consisting of toluene, methylene chlodde, chloroform and heptane.

6. A process for the purification of a cannabinoid comprising:
   esterifying the cannabinoid with at least one aryl sulfonyl halide in the presence of at least one base $R_5R_6R_7$ N, wherein $R_5$, $R_6$ and $R_7$ are lower alkyls of 1 to about 6 carbon atoms, to form a cannabinoid aryl sulfonate; and
   allowing the cannabinoid aryl sulfonate to crystallize, wherein the cannabinoid aryl sulfonate is crystalline and stable at room temperature under air.

7. The process according to claim 6, wherein the allowing of the cannabinoid aryl sulfonate to crystallize further includes adding at least one solvent and at least one seed crystal.

8. The process according to claim 7, wherein the at least one solvent is selected from the group consisting of methanol, heptane, hexane, t-butyl methyl ether, n-pentanol, n-butanol, isopropanol, isoburanol, ethanol, acetone, acetonitrile and isopropyl acetate.

9. The process according to claim 6, further includes recrystallizing the cannabinoid aryl sulfonate to purify the cannabinoid aryl sulfonate.

10. The process according to claim 6, wherein the cannabinoid is a naturally occurring component of cannabis.

11. The process according to claim 6, wherein the aryl of the at least one aryl sulfonyl halide is selected from the group consisting of benzene, alkyl substituted benzene, halogen substituted benzene, nitrobenzene, alkyloxy substituted benzene, substituted naphthyl compounds and unsubstituted naphthyl compounds.

12. A process for the purification of a cannabinoid comprising:
   esterifying the cannabinoid with at least one aryl sulfonyl halide in the presence of at least one base $R_5R_6R_7N$, wherein $R_5$, $R_6$ and $R_7$ are lower alkyls of 1 to about 6 carbon atoms, to form a cannabiniod aryl sulfonate;
   allowing the cannabinoid aryl sulfonate to crystallize; and,
   hydrolyzing the cannabinoid aryl sulfonate to recover the cannabinoid, wherein the cannabinoid aryl sulfonate is crystalline and stable at room temperature under air.

13. The process according to claim 12, further includes recrystallizing the cannabinoid aryl sulfonate to purify the cannabinoid aryl sulfonate.

14. The process according to claim 12, wherein the cannabinoid is a naturally occurring component of cannabis.

15. The process according to claim 12, wherein the aryl of the at least one aryl sulfonyl halide is selected from the group consisting of benzene, alkyl substituted benzene, halogen substituted benzene, nitrobenzene, alkyloxy substituted benzene, substituted naphthyl compounds and unsubstituted naphthyl compounds.

* * * * *